US 6,717,404 B2

(12) United States Patent
Prammer

(10) Patent No.: US 6,717,404 B2
(45) Date of Patent: Apr. 6, 2004

(54) SYSTEM AND METHODS FOR FORMATION EVALUATION WHILE DRILLING

(75) Inventor: Manfred Prammer, Downington, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/385,539

(22) Filed: Mar. 11, 2003

(65) Prior Publication Data

US 2003/0141869 A1 Jul. 31, 2003

Related U.S. Application Data

(63) Continuation of application No. 09/874,029, filed on Jun. 5, 2001, now Pat. No. 6,531,868, which is a continuation-in-part of application No. 09/552,160, filed on Apr. 18, 2000, now Pat. No. 6,242,913, which is a continuation of application No. 08/996,720, filed on Dec. 23, 1997, now Pat. No. 6,051,973.
(60) Provisional application No. 60/033,986, filed on Dec. 30, 1996.

(51) Int. Cl.[7] .................................................. G01V 3/00
(52) U.S. Cl. ........................................ 324/303; 324/300
(58) Field of Search ................................ 324/303, 300, 324/309, 318

(56) References Cited

U.S. PATENT DOCUMENTS

| 3,508,438 | A | * | 4/1970 | Alger et al. ................... 73/152 |
| 4,656,422 | A | * | 4/1987 | Vail et al. .................... 324/303 |
| 5,486,762 | A | * | 1/1996 | Freedman et al. ........... 324/303 |
| 6,051,973 | A | * | 4/2000 | Prammer ..................... 324/303 |
| 6,392,409 | B1 | * | 5/2002 | Chen .......................... 324/303 |
| 6,531,868 | B2 | * | 3/2003 | Prammer ..................... 324/303 |

FOREIGN PATENT DOCUMENTS

| DE | WO 92/10768 | * | 6/1998 |

* cited by examiner

*Primary Examiner*—Christopher W. Fulton
*Assistant Examiner*—Brij B. Shrivastav
(74) *Attorney, Agent, or Firm*—Jones Day

(57) ABSTRACT

A logging while drilling (LWD) and measuring while drilling (MWD) method and device are disclosed for reducing the sensitivity of NMR measurements to tool motions. The invention is based on NMR relaxation measurements determining longitudinal relaxation times T1 instead of the standard T2 measurements, and involves saturating a relatively wide sensitive region of the formation and processing NMR echo signals which originate approximately from the center of the sensitive region. In another aspect, the invention uses novel pulse sequences and processing algorithms to reduce the time for the relaxation measurement and to provide real-time transfer of data uphole.

25 Claims, 7 Drawing Sheets

SYSTEM AND METHODS FOR FORMATION EVALUATION WHILE DRILLING

This application is a continuation of application Ser. No. 09/874,029, filed Jun. 5, 2001 now U.S. Pat. No. 6,531,868, which is a continuation-in-part of application Ser. No. 09/552,160 filed Apr. 18, 2000, now U.S. Pat. No. 6,242,913, which is a continuation of application Ser. No. 08/996,720 filed Dec. 23, 1997, now U.S. Pat. No. 6,051,973, which is a continuation of provisional application No. 60/033,986 filed Dec. 30, 1996, which are incorporated herein by reference.

FIELD OF THE INVENTION

This invention is directed to a logging-while-drilling (LWD) and measurement-while-drilling (MWD) approach for obtaining nuclear magnetic resonance (NMR) data concerning petrophysical properties of a formation. More specifically, the invention is directed to an improved accuracy method and device for reducing the sensitivity of NMR measurements to tool motions, and real-time transmission over a slow data channel, such as mud pulsing for quick-look results at the surface.

BACKGROUND OF THE INVENTION

LWD and MWD systems are generally known in the art to make downhole measurements while a borehole is being drilled. Such systems measure various parameters and characteristics of the formation, such as its resistivity and the natural gamma ray emissions from the formation. Typically, signals which are representative of these measurements made downhole are relayed to the surface with a mud pulse telemetry device that controls the mud flow, encoding information in pressure pulses inside the drill string. The pulses travel upward through the mud to the surface, where they are detected and decoded so that the downhole measurements are available for observation and interpretation at the surface substantially in real time. In addition, it has also been found useful to provide a downhole computer with sufficient memory for temporarily storing these measurements until such time that the drill string is removed from the borehole.

U.S. Pat. No. 5,280,243 to Miller discloses an NMR apparatus and method of use for geophysical examination of a bore hole as it is being drilled. The patented apparatus is connected to the drill bit and follows it through the bore hole as it is being formed. In operation, the apparatus generates a gradient static magnetic field in a region of the bore hole adjacent the apparatus. This static field extends radially with respect to the longitudinal axis of the apparatus and has a generally uniform amplitude along the azimuth with respect to that axis. Next, a pulsed radio frequency magnetic field is generated to excite nuclei in a substantially cylindrical shell around the tool that defines in the formation a sensitive region extending along the length of the tool and having thickness of about 1 mm. Due to this relatively narrow sensitive region, standard wireline NMR relaxation time measurements are difficult to perform with this tool because lateral vibrations during the measurement time would reduce the accuracy of the measurement.

U.S. Pat. 5,557,201 to Kleinberg et al. discloses a pulsed NMR device in which the accuracy of the measurement with respect to lateral tool vibrations is enhanced by providing a larger sensitive region. This is achieved by a special tool architecture shown in FIGS. 2A–B, using two tubular permanent magnets 22 with same poles facing each other, and an antenna 26 positioned in the recess between the two magnets. In operation, this tool architecture provides a sensitive region in the formation which is larger laterally, but is greatly reduced along the borehole axis, because of the presence of a single stationary point in the formation. It is expected therefore that vertical tool motions would affect the accuracy of the tool measurements.

Current NMR LWD and MWD applications also suffer from the drawback that tool operators have no way of determining whether a portion of the formation which is being drilled at a given time is of interest or not. Typically, during the drilling process the measurement tool rotates along with the drill bit and is used in the more robust $T_1$ measurement mode. On the other hand, due to its better accuracy $T_2$ measurement mode is preferred for investigations of formation zones that are considered to be of higher interest. Such measurements are conducted while the drilling has been stopped, because the vibrations of the entire assembly during drilling interfere with the accuracy of the $T_2$ measurements. Thus, if the operator wishes to revisit interesting zones traversed by the borehole in the formation he has to compile a log of such zones in repeat the logging process separately.

Accordingly, it is perceived that there is a need for a system and method with improved sensitivity with respect to tool motions of pulsed NMR measurements using pulsed NMR tools. It is also perceived that there is a need for a system and method capable of providing real-time data concerning the properties of zones within the formation which are being investigated using LWD and MWD techniques.

SUMMARY OF THE INVENTION

The present invention concerns a novel method and device for formation evaluation while drilling a borehole using pulsed NMR tools with magnetic fields that are rotationally symmetric about the longitudinal axis of the borehole.

In a preferred embodiment, the method of the present invention is based on NMR relaxation time measurements determining longitudinal relaxation times $T_1$. In particular, the method comprises the steps of generating at least one radio frequency pulse covering a relatively wide range of frequencies to saturate the nuclear magnetization in a cylindrical volume around the tool; transmitting a readout pulse at a frequency near the center of the range of covered frequencies, the readout pulse following a predetermined wait time; applying at least one refocusing pulse following the readout pulse; receiving at least one NMR echo corresponding to the readout pulse; repeating the above steps for a different wait time to produce a plurality of data points on a $T_1$ relaxation curve; and processing the produced $T_1$ relaxation curve to derive petrophysical properties of the formation.

In another aspect, the invention is a method for making nuclear magnetic resonance (NMR) measurements of a geologic formation using a NMR logging tool, comprising the steps of: providing a static magnetic field in a volume of said formation; applying oscillating magnetic fields according to a pulse sequence $$\tau_i-\pi/2(+x)-[t_{cp}-\pi-t_{cp}-echo]_j-t_{cp}-\pi/2(-x)$$

where $\tau_i$ is a variable delay, and $i \geq 1$; $j \geq 1$; and +x and -x denote phases of the Larmor frequency of the carrier of the pulse with respect to a continuous wave Larmor frequency signal; $t_{cp}$ is the Carr-Purcell spacing; and measuring the induced NMR echo signals. an optimized pulse sequence for use in $T_1$ logging.

In yet another aspect, the invention is a method for real-time processing of downhole logging data, comprising the steps of: a) drilling a borehole into a geologic formation; b) while drilling the borehole, applying a first data acquisition sequence to determine substantially in real time at least one parameter of a zone in the formation being traversed; c) selecting a second data acquisition sequence based upon the at least one determined parameter; and e) applying the selected second data acquisition sequence to determine additional properties of said zone of the formation.

In another aspect, the invention is a method for making nuclear magnetic resonance (NMR) measurements of a geologic formation using an NMR logging tool, comprising the steps of: applying oscillating magnetic fields according to a first pulse sequence $$\tau_i-\pi/2(+x)-[t_{cp}-\pi-t_{cp}-echo]_j-t_{cp}-\pi/2(-x)$$

where $\tau_i$ is a variable delay, and $i \geq 1$; $j \geq 1$; and +x and −x denote phases of the Larmor frequency of the carrier of the pulse with respect to a continuous wave Larmor frequency signal; $t_{cp}$ is the Carr-Purcell spacing; applying one or more times a chirped pulse sequence, comprising a radio frequency (RF) pulse covering a relatively wide range of frequencies to saturate nuclear magnetization in a volume within the geologic formation and a readout pulse sequence at a frequency within the range of covered frequencies, the readout pulse sequence following a predetermined wait time after the saturation pulse; receiving NMR echo signals corresponding to the first pulse sequence and to the one or more chirped pulse sequence; and processing the received NMR echo signals to determine properties of the geologic formation.

Additional aspect of the invention are described in further detail below.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

DETAILED DESCRIPTION

Figure 1A:
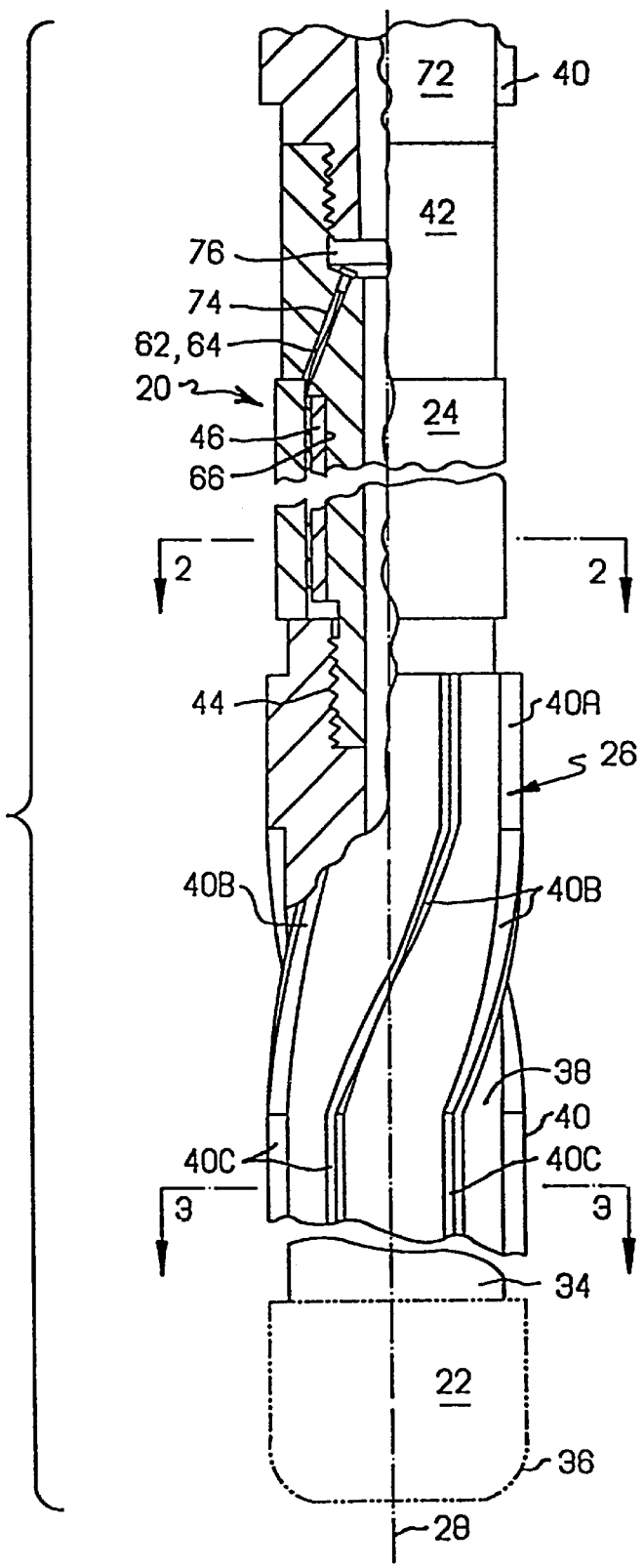
FIG. 1A shows a side elevational view, partly in section, of the lower end of the apparatus disclosed in U.S. Pat. No. 5,280,243.
Figure 1B:
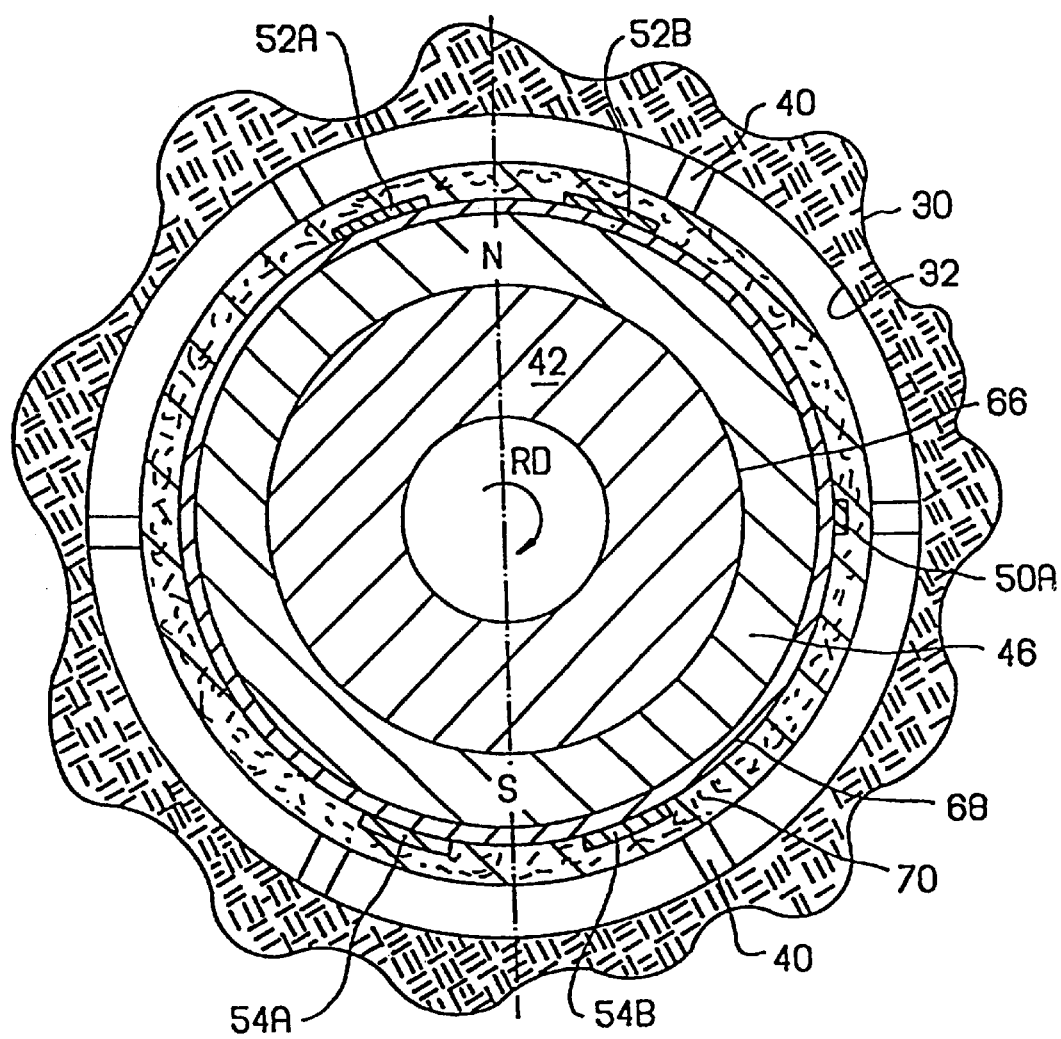
FIG. 1B is an enlarged sectional view taken along the line 2—2 in FIG. 1A.
Figure 2A:
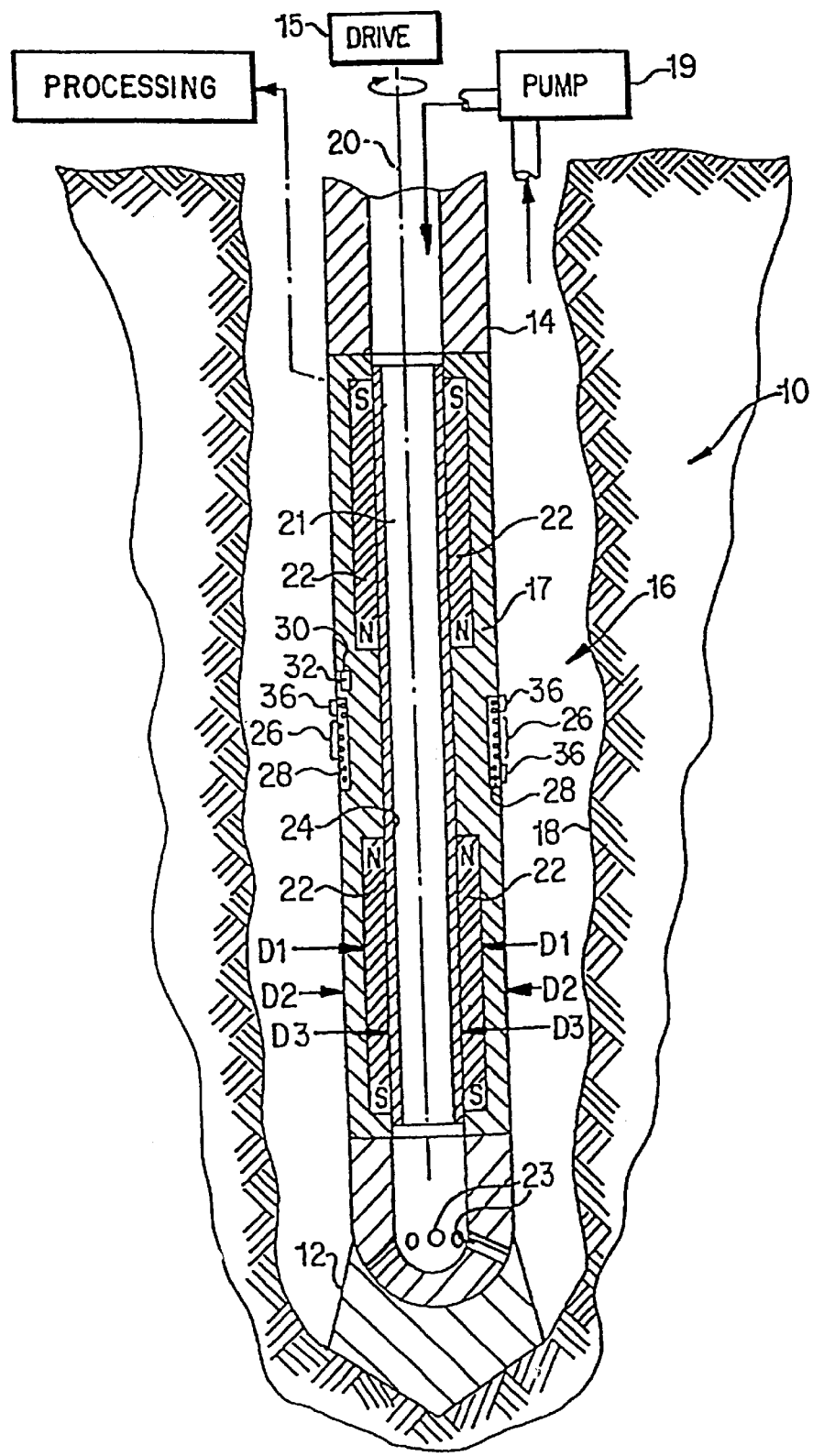
FIG. 2A shows a cross-section of a tool for pulsed NMR formation evaluation disclosed in U.S. Pat. No. 5,557,201.
Figure 2B:
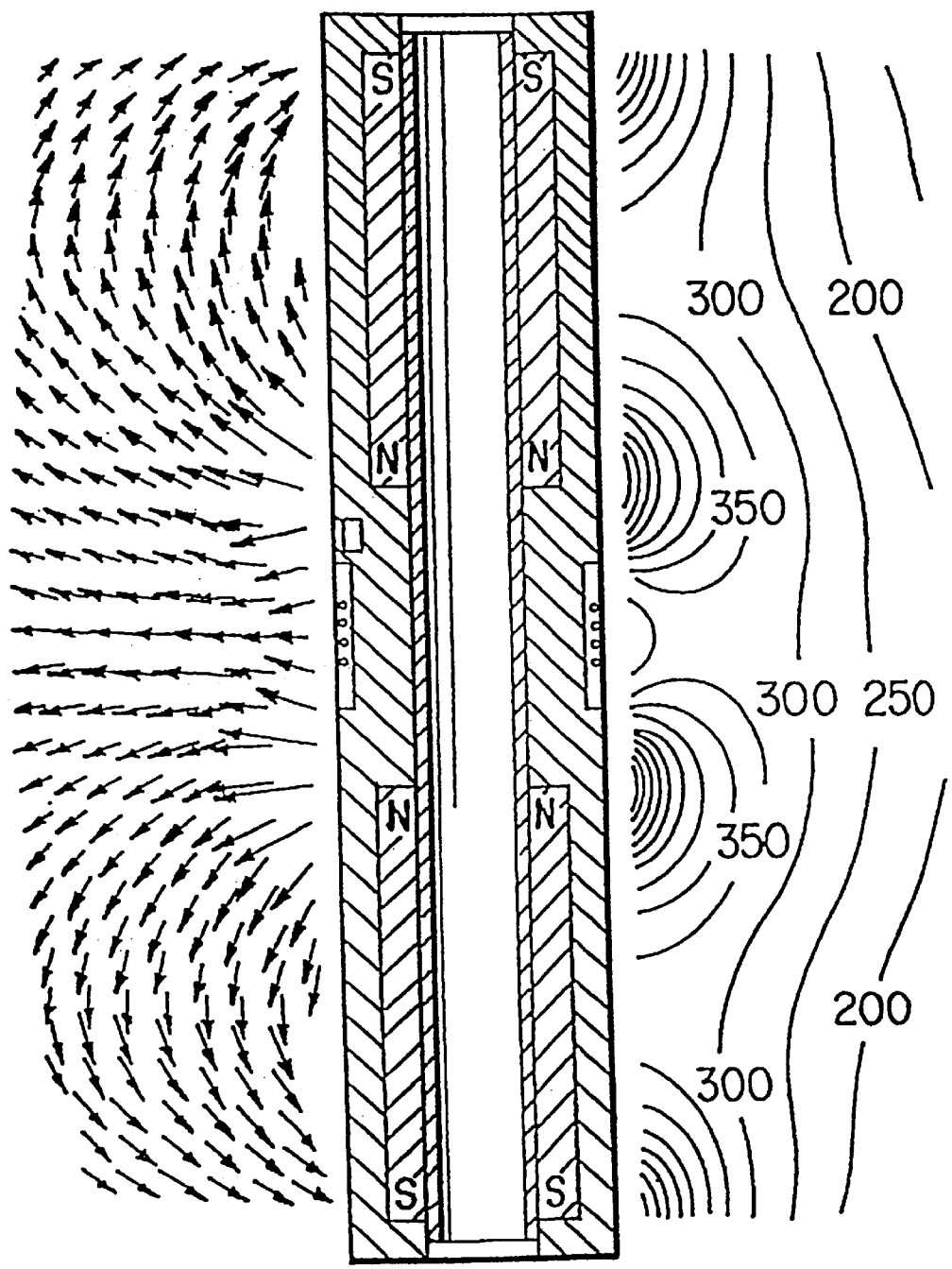
FIG. 2B shows a static field in a vertical plane of the same tool.

The description of the preferred embodiment of the method of the present invention is made with reference to the tool disclosed in U.S. Pat. No. 5,280,243 to Miller, owned by the assignee of the present application. The content of the Miller patent is expressly incorporated herein for all purposes. FIGS. 1A and 1B respectively show a side elevational view, partly in section, of the lower end of the Miller tool and an enlarged sectional view taken along the line 2—2 in FIG. 1A. It should be noted, however, that the method of the present invention can also be used with any tool that generates a rotationally symmetric magnetic field including, for example, the tool disclosed in U.S. Pat. No. 5,557,201 to Kleinberg, illustrated in FIGS. 2A and 2B.

The method of the present invention is based on NMR relaxation time measurements determining longitudinal relaxation times T1, instead of transversal relaxation times T2 that are typically used by a wireline tool. In particular, the method takes advantage of the magnetic field gradient which can be approximated in the proximity of the sensitive volume as a linear fall-off of the magnetic field strength (and also of NMR resonance frequency) in the radial direction.

In a preferred embodiment, at the start of a measurement, one or more radio frequency pulses covering a relatively wide range of frequencies, or using one or more pulses which are frequency swept, are transmitted to saturate the nuclear magnetization in a cylindrical volume around the tool. The range of frequencies can be, for example, 50–100 kHz and is covered in a specific embodiment using a rapid succession of short radio frequency pulses similar to the first pulse in a standard CPMG pulse sequence, or using a single long pulse in a frequency sweep. Changing the range of frequencies used in this step varies the position and the width of the sensitive region in the formation. In a specific embodiment using the Miller tool, a frequency range between 50 and 100 kHz saturates the nuclear magnetization in a cylindrical volume around the tool, where the cylinder has a typical diameter of 14", a height of 24", and thickness of between about ½" to 1".

Following the step of saturation, which typically takes about 1 ms, in accordance with the present invention a readout pulse is transmitted at a frequency near the center of the range of covered frequencies. In alternative embodiments one or more subsequent readout pulses can also be used. In accordance with the present invention, a readout pulse sequence is comprised of a 90° pulse followed by data acquisition, or of a 90° pulse followed by a 180° pulse, followed by data acquisition, where the steps of applying a 180° pulse and data acquisition can be repeated. The readout pulse sequence generally follows a predetermined wait time, as explained in more detail below. In a specific embodiment the readout pulse sequence is transmitted at a center frequency of about 500 kHz, and is followed by one or more refocusing pulses.

Following the readout pulse(s), corresponding NMR echo signals are received, amplified and stored for further processing. Preferably, only the first, the second echo or a combination thereof is retained. In accordance with a preferred embodiment, the amplitude of the retained echo signal is interpreted as the level of nuclear magnetization present after the particular wait time. In the particular example considered above, the center frequency of the NMR echo signals corresponds to about 14" diameter of investigation.

The measurement process described above is repeated for a series of increasing wait times the values of which can, for example, be equally distributed on a logarithmic scale. In a specific embodiment, wait times are stepped through the values 1 ms, 3 ms, 10 ms, 30 ms, 100 ms, 300 ms, 1000 ms and 3000 ms, and the measurement results are stacked to produce several data points on a multi-component T1 relaxation curve. A data point corresponding to the longest wait time is obtained by a readout pulse sequence which is not preceded by a saturation pulse.

Finally, in accordance with the present invention the produced T1 relaxation curve is used to derive petrophysical properties of the formation, as known in the art. In particular, the resultant T1 relaxation curve is processed to extract the dominant T1 relaxation modes, from which amounts of bound water, free water and hydrocarbons are estimated. The characteristic T1 times of the surface-wetting phase can also be used to estimate formation pore size distributions and formation permeability.

Figure 3:
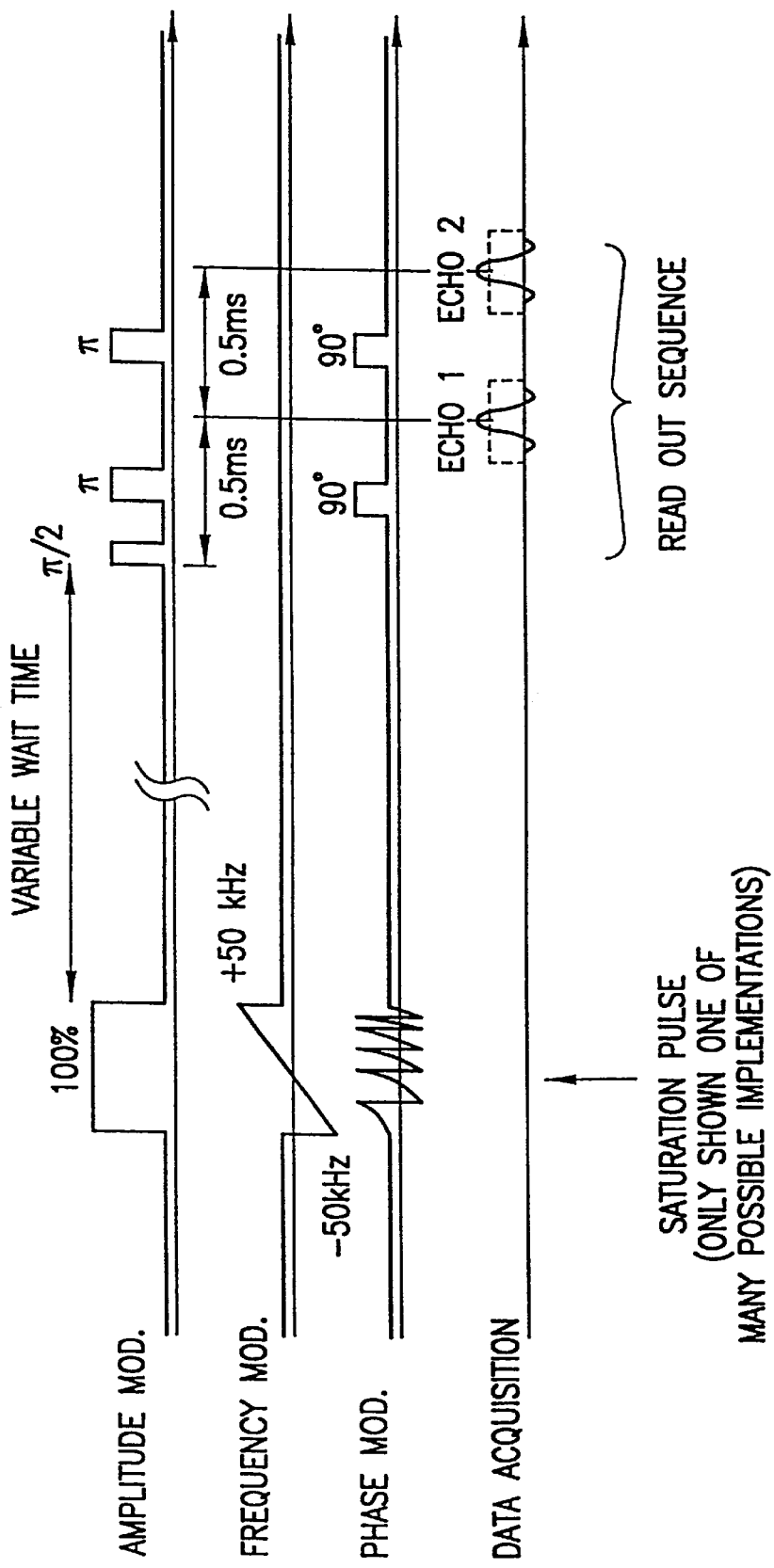
FIG. 3 illustrates a motion-insensitive pulse sequence used in a specific embodiment in accordance with the present invention.

It should be noted that since the readout pulse and the signal acquisition have a much smaller bandwidth, typically 5–10 kHz vs. 50–100 kHz saturation bandwidth, the measurement results obtained using the above-described method are less sensitive to lateral motions of the tool, and in particular are not affected by lateral displacements during the wait time period which do not exceed ¼"–½". An illustration of a pulse sequence used in specific embodiment of the present invention is shown in FIG. 3.

In accordance with another preferred embodiment of the present invention, the tool used to make the measurements can be fitted with accelerometers, such as those manufactured by Analog Devices, to monitor peak acceleration values along all three axis during the measurement interval and magnetometers. Measurements, during which the peak accelerations indicate that the tool may have been displaced by more than allowable by the extent of the saturation region, are discarded before stacking to further improve the accuracy of the proposed method.

In accordance with another preferred embodiment, the tool is further fitted with hardened steel stand-offs, which, in an in-gauge borehole, allow lateral tool displacements only within the range given by the saturation width. Naturally, the tool may further be provided with accelerometers, as described above, for further accuracy.

Figure 4:
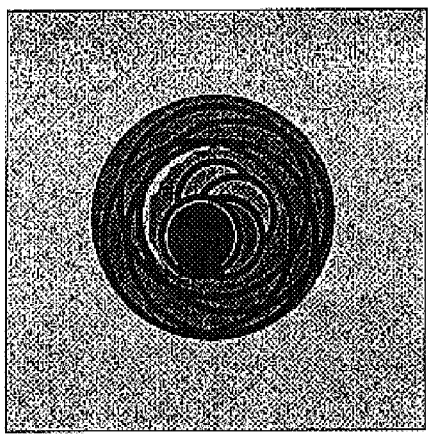
FIG. 4 is a top view into a borehole with an inserted tool and illustration of the area covered by the saturation pulse and the annulus used for readout portion of the pulse sequence shown in FIG. 3.

The above method of determination of $T_1$ in accordance with this invention is based on determining data points on a $T_1$ polarization recovery curve. The broadband, frequency-swept chirp pulse shown in FIG. 3 is issued to saturate nuclear magnetization in a wide annulus around the tool. After a given recovery time, two short pulses are issued to trigger a spin echo, which is digitized and quantified. FIG. 4 illustrates in a light-gray annulus the volume reached by the chirp pulse, while the dark-gray rings indicate possible positions for the readout volume. In this figure the tool is shown inside the borehole. As long as the readout volume falls anywhere within the band prepared by the chirp pulse, a valid reading is obtained. Although the measurement itself may take seconds, the motion and displacement of the drill string and the attached NMR tool within this time period is practically immaterial.

As noted above, in a specific embodiment, the recovery times are stepped, for instance, through the series of 1 ms, 3 ms, 10 ms, 30 ms, 100 ms, 300 ms, 1000 ms, and 3000 ms. The echo amplitudes from these experiments link up to a magnetization recovery curve, from which a $T_1$ time distribution can be derived. As known, the area under the distribution is indicative of the total porosity (subject to variations in hydrogen density) and the distribution itself is used to quantify the amount of clay-bound water, capillary-bound water and free fluids (water, gas, oil).

In another aspect, the invention is an improvement allowing the sequence of steps outlined above to be repeated rapidly so as to reduce the overall measurement time and/or increase the number of data points collected. It will be appreciated that in order to achieve good measurement statistics, the cycle through all recovery times should be repeated as fast as possible. Analysis of the measurement sequence shows that most of the time is spent acquiring data for the longest recovery times. Based on this observation, in accordance with another aspect of the invention, two methods can be used individually or preferably in combination to speed up the process. Accordingly, in a first embodiment, speeding up of the process is based on a random selection of a new measurement volume. In a second embodiment, use is made of a forced magnetization recovery pulse sequence to make maximum use of the existing formation magnetization. The preferred third embodiment uses a combination of the first and second methods in a manner discussed in more detail below.

Figure 5:
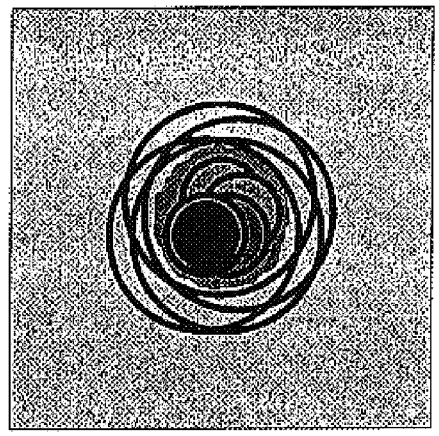
FIG. 5 is another top view into a borehole with an inserted tool, illustrating how the random motion of the tool within the borehole can be used advantageously to improve the speed of the measurement.

In accordance with the first embodiment, random selection of a new measurement volume is applied. The method makes use of the random lateral motion of the drill string during normal operation. In essence, the method is based on using the undesirable under normal conditions motion of the tool within the borehole in order to change the volume saturated with nuclear magnetization around the tool. Without the use of the chirp pulse discussed above, only a narrow annulus is touched by each measurement. Therefore, within a few hundred milliseconds after each measurement the sensitive volume of the tool moves to a fresh, untouched annulus and the measurement can be repeated much faster than dictated by $T_1$ recovery alone. The principle is illustrated in FIG. 5, which shows a top view of the borehole without the use of an explicit saturation pulse. In a preferred embodiment, the longest wait-time data points may be are acquired using this approach, in which repeated measurements of full magnetization (shown in dark-grey) are possible by letting the sensitive volume randomly wander within the formation. The remaining data points are obtained as discussed above.

Figure 6:
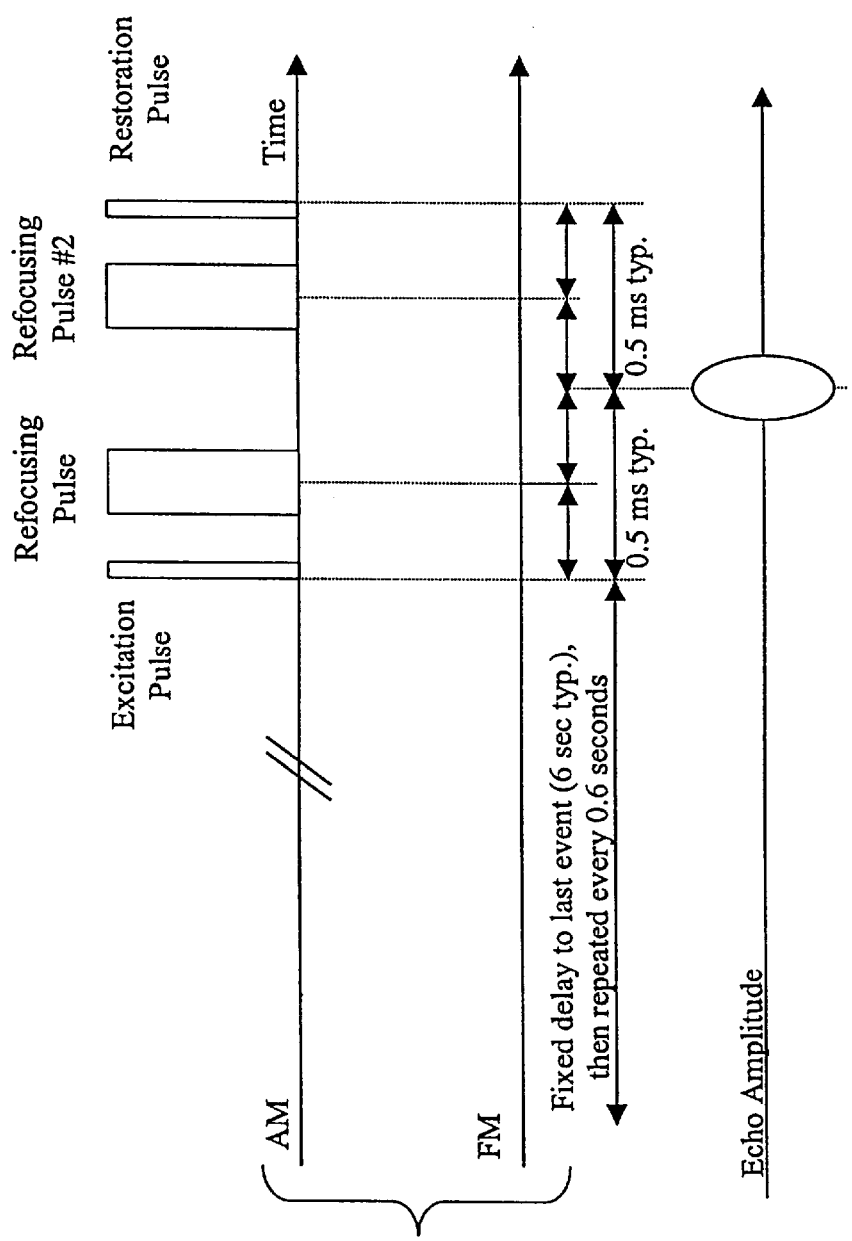
FIG. 6 is an illustration of a forced recovery pulse sequence used in another embodiment of the present invention.

In accordance with the second embodiment, another method can be used, referred to as forced magnetization recovery. This technique is known in the context of MR imaging, but to the best of the applicant's knowledge has not been applied in downhole NMR measurements. The basic forced magnetization recovery pulse sequence used in accordance with the present invention is shown in FIG. 6. In particular, following an initial long delay, that may be set in a typical application to 6 sec., a combination of $(\pi/2)x$ pulse and $(\pi)y$ pulse trigger a spin echo. The echo is refocused using a second $(\pi)y$ pulse. In a preferred embodiment, the following signal acquisition window is replaced by a $(\pi/2)-x$ pulse that performs the opposite function of the initial $(\pi/2)x$ pulse by flipping back magnetization into the z direction. Experiments have shown that approximately 80%–90% of the initial magnetization can be recovered in practice. This equates to time savings of two $T_1$ time constants in this preferred embodiment. It will be appreciated that other pulse sequences can be used in practice, such as replacing a signal acquisition window with a $(\pi/2)-x$ pulse following the second, or subsequent echos. It will be apparent to a person of skill in the art that different timing can be used in various practical applications as well. The forced magnetization recovery method in accordance with the present invention, makes optimum use of the existing polarization.

Finally, in accordance with a preferred embodiment of the invention, a combination of the above two methods can be applied using a sequence optimized in accordance with the present invention for $T_1$ logging, described as follows:

(1) apply an initial long delay to equilibrate the hydrogen magnetization. In a preferred embodiment 6000 ms can be used for the delay;

(2) apply the forced-recovery sequence as shown in FIG. 6. In a preferred embodiment, the forced-recovery sequence is repeated 8 times every 600 ms. It will be appreciated that no chirp pulse is issued at this time;

(3) repeatedly apply the chirped sequence according to FIG. 3, using different saturation recovery times, as dictated from the desired data points on the $T_1$ curve.

In a specific embodiment, the chirped sequence is applied as follows:

(a) a chirped sequence repeated 8 times and using a saturation-recovery time of 300 ms;

(b) a chirped sequence repeated 16 times and using a saturation-recovery time of 100 ms;

(c) a chirped sequence repeated 16 times and using a saturation-recovery time of 30 ms;

(d) a chirped sequence repeated 64 times and using a saturation-recovery time of 10 ms; and (e) a chirped sequence repeated 64 times and using a saturation-recovery time of 1 ms.

With the timing illustrated in FIGS. 3, 6 and method step (1), this entire sequence takes 16 seconds to execute. CPMG phase cycling (phase alternation) is embedded within the repeats. It will be appreciated that without departing from the spirit of this invention in practice various modifications may be used of the number of times each sequence is repeated, or the specific recovery times, or the sequence in which data points for different recovery times are acquired.

In accordance with another aspect of the invention, the motion of the tool can be used for automatic selection of a $T_1$ or $T_2$ measurement mode. As noted above, in a preferred embodiment, the tool contains accelerometers and magnetometers that sense the presence of motion. For example, it is well known that the rotation of the tool in LWD mode can be detected by magnetometers. Acceleration and magnetic induction signals can be obtained in accordance with the present invention from micro-machined silicone accelerometers, as distributed by Silicon Designs with a bandwidth of 5 kHz and magnetoresistive sensors (magnetometers) from Honeywell (Model HMC1002). If the sensors detect motion that corresponds to the rotation of the drill bit, in a preferred embodiment of the invention a $T_1$ measurement mode is activated. If no motion is detected, the tool enters $T_2$ measurement mode. The automatic selection of the measurement mode can be implemented in a preferred embodiment using the real-time data transfer options described below.

Real-Time Data Transfer

As noted above, signals which are representative of measurements made downhole can be relayed to the surface with a mud pulse telemetry device that controls the mud flow, encoding information in pressure pulses inside the drill string. The pulses travel upward through the mud to the surface, where they are detected and decoded so that the downhole measurements are available for observation and interpretation at the surface substantially in real time. As an alternative, it is known in the art to provide a downhole processor with sufficient memory for temporarily storing measurements until such time that the drill string is removed from the borehole. Mud pulse systems of this type are discussed, for example, in U.S. Pat. Nos. 5,586,083 and 5,586,084, both assigned to the assignee of the present application, which are hereby incorporated by reference for all purposes.

The transfer of real-time data to the surface is handicapped by the very slow data channel available as a fraction of the throughput of the mud pulsing system. Rates of several bit/s are typical. In accordance with the present invention, two methods of addressing this issue can be used in different embodiments.

Downhole $T_1$ inversion. In accordance with a first embodiment, data from several complete cycles can be averaged into a small number of data points. In a preferred embodiment, data from 4 complete cycles of the $T_1$ measurement optimized sequence described above (corresponding to 64 seconds) are averaged into 6 data points. A smaller or larger number of points can be used in alternative embodiment. The data points obtained in the preferred embodiment correspond, for example, to recovery times of 6000, 300, 100, 30, 10 and 1 ms. The corresponding saturation-recovery curve is transformed into a series of $T_1$ components using a fixed set of basis functions. The time constants for these basis functions range from 1 ms to 10 s. Selected statistics, for example, the total area under the $T_1$ curve (associated with the porosity of the formation), the geometric mean $T_1$ time (associated with the permeability of the formation), and others, are transmitted uphole and used for a preview of porosity, estimated bound water and free fluid volumes and permeability.

Uphole $T_1$ inversion. In accordance with a second embodiment, the averaged data points themselves are transmitted uphole and processed there. It will be appreciated that not every data point is equally important. Therefore, in some applications it may be sufficient to use for the uphole fit only the fastest (1 ms), a medium-fast, and the slowest data points.

A person of skill in the art will appreciate that in different practical applications either downhole or uphole inversions using different numbers of data points may be used.

The foregoing description of the preferred embodiments of the present invention has been presented for purposes of illustration and description. It is not intended to be exhaustive nor to limit the invention to the precise form disclosed. Many modifications and variations will be apparent to those skilled in the art. The embodiments were chosen and described in order to best explain the principles of the invention and its practical applications, thereby enabling others skilled in the art to understand the invention. Various embodiments and modifications that are suited to a particular use are contemplated. It is intended that the scope of the invention be defined by the accompanying claims and their equivalents.

What is claimed is:

1. A method for making nuclear magnetic resonance (NMR) measurements of a geologic formation using an NMR logging tool, comprising the steps of:

(a) applying downhole one or more forced magnetization recovery pulse sequences;

(b) applying at least one $T_1$ saturation-recovery sequence following the one or more forced magnetization recovery pulse sequences;

(c) receiving NMR echo signals in response to pulse sequences applied in steps (a) and (b); and (d) processing the received NMR echo signals to determine properties of the geologic formation.

2. The method of claim 1, wherein the one or more forced magnetization recovery pulse sequences are given by the expression:

$$[\tau_i\text{-}\pi/2(+x)\text{-}[t_{cp}\text{-}\pi\text{-}t_{cp}\text{-}echo]_j\text{-}t_{cp}\text{-}\pi/2(-x)]_k$$

where $\tau_i$ is a variable delay, and $i \geq 1$; $j \geq 1$; $k \geq 1$; and +x and −x denote phases of the Larmor frequency of the carrier of the pulse with respect to a continuous wave Larmor frequency signal; $t_{cp}$ is the Carr-Purcell spacing, wherein the echo train defined by $t_{cp}$ and j in the sequence is shorter than the longest expected characteristic signal decay time component $T_2$.

3. The method of claim 2, wherein the phase of all $\pi$ pulses is y.

4. The method of claim 2, wherein the phase of all $\pi$ pulses is x.

5. The method of claim 2, wherein for $k \geq 2$ the index i is held fixed.

6. The method of claim 2, wherein for $k \geq 2$ the index i is varied, resulting in variable delay $\tau_i$ times.

7. The method of claim 6, wherein i=k.

8. The method of claim 2, wherein $\tau_1 \gg \tau_i$, where i=2, 3, ..., N and N is an integer.

9. The method of claim 8, wherein $\tau_1 \geq 1$ second.

10. The method of claim 1, wherein step (b) of applying at least one $T_1$ saturation-recovery sequence comprises the step of:

applying one or more times a chirped pulse sequence, comprising
a radio frequency (RF) pulse covering a relatively wide range of frequencies to saturate nuclear magnetization in a volume within the geologic formation and a readout pulse sequence at a frequency within the range of covered frequencies, the readout pulse sequence following a predetermined wait time after the saturation pulse.

11. The method of claim 10, wherein the chirped sequence is repeated using different saturation recovery times.

12. The method of claim 11, wherein the selection of different saturation recovery times is made based on desired data points on a $T_1$ relaxation curve.

13. The method of claim 12, wherein the chirped sequence is repeated using saturation recovery times including two or more of the following: 1 ms, 10 ms, 30 ms, 100 ms, 300 ms, 1000 ms, 3000 ms.

14. The method of claim 10, wherein the range of frequencies is covered using a rapid succession of short radio frequency pulses.

15. The method of claim 10, wherein the range of frequencies is covered using a single pulse in a frequency sweep.

16. The method of claim 1 further comprising the step of monitoring the motion of the tool with respect to the borehole.

17. The method of claim 16, wherein the step of processing comprises discarding echo signals obtained during measurement intervals when motion tool acceleration values exceed predetermined threshold.

18. The method of claim 1, wherein steps (a), (b) and (c) are performed concurrently with the step of drilling a borehole in said geologic formation.

19. The method of claim 1, wherein the step of processing comprises computation of $T_1$ relaxation times.

20. The method of claim 1, wherein the phase of the $\pi$ pulses is alternated between +y and −y for incremental values of the index i.

21. A system for making nuclear magnetic resonance (NMR) measurements of a geologic formation using an NMR logging tool, comprising the steps of:

(a) means for applying downhole one or more forced magnetization recovery pulse sequences;

(b) means for applying at least one $T_1$ saturation-recovery sequence following the one or more a forced magnetization recovery pulse sequences;

(c) means for receiving NMR echo signals in response to NMR pulse sequences; and (d) means for processing the received NMR echo signals to determine properties of the geologic formation.

22. The system of claim 21, wherein the one or more a forced magnetization recovery pulse sequences are given by the expression:

$$[\tau_i - \pi/2(+x) - [t_{cp} - \pi - t_{cp} - \text{echo}]_j - t_{cp} - \pi/2(-x)]_k$$

where $\tau_i$ is a variable delay, and $i \geq 1$; $j \geq 1$; $k \geq 1$; and +x and −x denote phases of the Larmor frequency of the carrier of the pulse with respect to a continuous wave Larmor frequency signal; $t_{cp}$ is the Carr-Purcell spacing, wherein the echo train defined by $t_{cp}$ and j in the sequence is shorter than the longest expected characteristic signal decay time component $T_2$.

23. The system of claim 21, wherein the means for applying at least one $T_1$ saturation-recovery sequence comprises:

means for applying one or more times a chirped pulse sequence, comprising
a radio frequency (RF) pulse covering a relatively wide range of frequencies to saturate nuclear magnetization in a volume within the geologic formation and a readout pulse sequence at a frequency within the range of covered frequencies, the readout pulse sequence following a predetermined wait time after the saturation pulse.

24. The system of claim 21 further comprising the step of monitoring the motion of the tool with respect to the borehole.

25. The system of claim 21 further comprising a drill bit for drilling a borehole in said geologic formation, and at least the means in (a), (b) and (c) are capable of operating concurrently with the drilling of a borehole.

* * * * *